(12) United States Patent
Tokuda et al.

(10) Patent No.: US 11,150,252 B2
(45) Date of Patent: Oct. 19, 2021

(54) METHOD FOR MEASURING PHOSPHORYLATED TAU PROTEIN

(71) Applicants: NATIONAL INSTITUTES FOR QUANTUM AND RADIOLOGICAL SCIENCE AND TECHNOLOGY, Chiba (JP); SYSMEX CORPORATION, Kobe (JP)

(72) Inventors: Takahiko Tokuda, Kyoto (JP); Harutsugu Tatebe, Kyoto (JP)

(73) Assignees: SYSMEX CORPORATION, Kobe (JP); National Institutes for Quantum and Radiological Science and Technology, Chiba (JP)

( * ) Notice: Subject to any disclaimer, the term of this patent is extended or adjusted under 35 U.S.C. 154(b) by 0 days.

(21) Appl. No.: 16/049,028

(22) Filed: Jul. 30, 2018

(65) Prior Publication Data

US 2019/0033328 A1    Jan. 31, 2019

(30) Foreign Application Priority Data

Jul. 31, 2017   (JP) .............................. JP2017-148274

(51) Int. Cl.
    *G01N 33/68*    (2006.01)
    *G01N 33/543*   (2006.01)
(52) U.S. Cl.
    CPC ... *G01N 33/6896* (2013.01); *G01N 33/54306* (2013.01); *G01N 33/54313* (2013.01); *G01N 2440/14* (2013.01); *G01N 2800/2821* (2013.01)

(58) Field of Classification Search
    None
    See application file for complete search history.

(56) References Cited

U.S. PATENT DOCUMENTS

| 6,008,024 A | 12/1999 | Vandermeeren et al. |
| 6,500,674 B1 | 12/2002 | Vandermeeren et al. |
| 10,087,245 B2 | 10/2018 | Lafaye et al. |

(Continued)

FOREIGN PATENT DOCUMENTS

| JP | 9-506771 A | 7/1997 |
| JP | 2000-34300 A | 2/2000 |

(Continued)

OTHER PUBLICATIONS

Chen "Enhancement and destruction of antibody function by somatic mutation: unequal occurrence is controlled by V gene combinatorial associations" EMBO 14(12):2784-2794 1995 (Year: 1995).*

(Continued)

*Primary Examiner* — Adam Weidner
(74) *Attorney, Agent, or Firm* — Sughrue Mion, PLLC

(57) ABSTRACT

Disclosed is a method for measuring phosphorylated tau protein in a biological sample collected from a subject, comprising the steps of: preparing a measurement sample containing a non-capture bead and a capture bead to which an immune complex is bound, by forming the immune complex of the phosphorylated tau protein in the biological sample, a capture antibody and a detection antibody on the capture bead, in the presence of the non-capture bead; and detecting a signal derived from the immune complex in the measurement sample.

13 Claims, 5 Drawing Sheets

(56) References Cited

U.S. PATENT DOCUMENTS

| | | | |
|---|---|---|---|
| 10,538,582 | B2 | 1/2020 | Lafaye et al. |
| 2003/0138972 | A1 | 7/2003 | Vandermeeren et al. |
| 2004/0038430 | A1 | 2/2004 | Vandermeeren et al. |
| 2014/0302532 | A1* | 10/2014 | Wilson ............... G01N 33/6896 435/7.92 |
| 2016/0116488 | A1* | 4/2016 | Lehmann ........... G01N 33/6896 506/9 |
| 2017/0058022 | A1 | 3/2017 | Lafaye et al. |
| 2019/0077853 | A1 | 3/2019 | Lafaye et al. |
| 2020/0165329 | A1 | 5/2020 | Lafaye et al. |

FOREIGN PATENT DOCUMENTS

| | | | |
|---|---|---|---|
| JP | 2017-506068 A | | 3/2017 |
| WO | WO 2011109364 | * | 3/2010 |
| WO | 2016/115256 A1 | | 7/2016 |

OTHER PUBLICATIONS

Kussie "A Single Engineered Amino Acid Substitution Changes Antibody Fine Specificity" J immunol 152(1):146-52 1994 (Year: 1994).*

Shashank Shekhar, et al., "Estimation of Tau and Phosphorylated $Tau_{181}$ in Serum of Alzheimer's Disease and Mild Cognitive Impairment Patients", PLOS One, Jul. 26, 2016, pp. 1-10, vol. 11, No. 7.

Office Action, dated Jun. 15, 2021, issued by the Japanese Patent Office in counterpart Japanese Application No. 2017-148274.

\* cited by examiner

METHOD FOR MEASURING PHOSPHORYLATED TAU PROTEIN

CROSS REFERENCE TO RELATED APPLICATIONS

This application claims priority from prior Japanese Patent Application No. 2017-148274 filed on Jul. 31, 2017, entitled "Method for measuring phosphorylated tau protein", the entire contents of which are incorporated herein by reference.

TECHNICAL FIELD

The present invention relates to a method for measuring phosphorylated tau protein, and a method for acquiring information on whether or not a subject suffers from Alzheimer's disease, based on measured values acquired by the above measurement method. The present invention also relates to a device for measuring phosphorylated tau protein, and a device for acquiring information on whether or not a subject suffers from Alzheimer's disease, based on measured values acquired by the above measurement method. Furthermore, the present invention relates to a computer program for measuring phosphorylated tau protein, and a computer program for acquiring information on whether or not a subject suffers from Alzheimer's disease, based on measured values acquired by the measurement method.

BACKGROUND

Phosphorylated tau protein is thought to be useful as a biomarker of nervous system diseases such as Alzheimer's disease. PLoS One. 2016 Jul. 26; 11(7):e0159099. doi: 10.1371/journal.pone.0159099. eCollection 2016 describes that phosphorylated tau protein in serum was measured by surface plasmon resonance technology (SPR) method, and the phosphorylated tau protein in serum was higher in Alzheimer's disease than in the control group and mild cognitive impairment.

WO 2016/115256 A describes a digital ELISA method with more improved accuracy than the conventional digital ELISA (Enzyme-Linked ImmunoSorbent Assay) method.

SUMMARY

The scope of the present invention is defined solely by the appended claims, and is not affected to any degree by the statements within this summary.

A first embodiment relates to a method for measuring phosphorylated tau protein in a biological sample collected from a subject, including steps of: preparing a measurement sample containing a non-capture bead and a capture bead to which an immune complex is bound, by forming the immune complex of the phosphorylated tau protein in the biological sample, a capture antibody and a detection antibody on the capture bead, in the presence of the non-capture bead, and detecting a signal derived from the immune complex in the measurement sample, wherein the non-capture bead does not bind to the immune complex, at least one of the detection antibody and the capture antibody specifically recognizes the phosphorylated tau protein, the epitope of the capture antibody is different from the epitope of the detection antibody, and the number ratio of the capture beads and the non-capture beads mixed in the preparation step is 1.5 or more of the non-capture beads to 1 of the capture beads.

A second embodiment relates to a method for acquiring information on whether or not the subject suffers from Alzheimer's disease, based on the intensity of a signal obtained by the method as defined in the first embodiment.

A third embodiment relates to a device 20 for measuring phosphorylated tau protein in a biological sample collected from a subject, the device 20 comprising a processing unit 21, wherein the processing unit 21 obtains a signal derived from an immune complex, for a measurement sample containing a non-capture bead and a capture bead to which the immune complex is bound, prepared by forming the immune complex of the phosphorylated tau protein in the biological sample, a detection antibody and a capture antibody on the capture bead, in the presence of the non-capture bead, the non-capture bead does not bind to the immune complex, at least one of the detection antibody and the capture antibody specifically recognizes the phosphorylated tau protein, the epitope of the capture antibody is different from the epitope of the detection antibody, and the number ratio of the capture beads and the non-capture beads mixed in the preparation of the measurement sample is 1.5 or more of the non-capture beads to 1 of the capture beads.

A fourth embodiment relates to a device 50 for acquiring information on whether or not a subject is Alzheimer's disease, based on the intensity of a signal derived from phosphorylated tau protein in a biological sample collected from the subject, the device 50 comprising a processing unit 51, wherein the processing unit 51 obtains a signal derived from an immune complex, for a measurement sample containing a non-capture bead and a capture bead to which the immune complex is bound, prepared by forming the immune complex of the phosphorylated tau protein in the biological sample, a detection antibody and a capture antibody on the capture bead, in the presence of the non-capture bead, the non-capture bead does not bind to the immune complex, at least one of the detection antibody and the capture antibody specifically recognizes the phosphorylated tau protein, the epitope of the capture antibody is different from the epitope of the detection antibody, the number ratio of the capture beads and the non-capture beads mixed in the preparation of the measurement sample is 1.5 or more of the non-capture beads to 1 of the capture beads, and information on whether or not the subject is Alzheimer's disease is acquired, based on the intensity of the signal.

A fifth embodiment relates to a computer program for measuring phosphorylated tau protein that makes a computer execute a step of obtaining a signal derived from an immune complex, for a measurement sample containing a non-capture bead and a capture bead to which the immune complex is bound, prepared by forming the immune complex of the phosphorylated tau protein in the biological sample, a detection antibody and a capture antibody on the capture bead, in the presence of the non-capture bead, wherein the biological sample is collected from a subject, the non-capture bead does not bind to the immune complex, at least one of the detection antibody and the capture antibody specifically recognizes the phosphorylated tau protein, the epitope of the capture antibody is different from the epitope of the detection antibody, and the number ratio of the capture beads and the non-capture beads mixed in the preparation of the measurement sample is 1.5 or more of the non-capture beads to 1 of the capture beads.

A sixth embodiment relates to a computer program for acquiring information on whether or not a subject is Alzheimer's disease, that makes a computer execute a step of obtaining a signal derived from an immune complex, for a measurement sample containing a non-capture bead and a capture bead to which the immune complex is bound, prepared by forming the immune complex of the phosphorylated tau protein in the biological sample, a detection antibody and a capture antibody on the capture bead, in the presence of the non-capture bead, wherein the non-capture bead does not bind to the immune complex, at least one of the detection antibody and the capture antibody specifically recognizes the phosphorylated tau protein, the epitope of the capture antibody is different from the epitope of the detection antibody, the number ratio of the capture beads and the non-capture beads mixed in the preparation of the measurement sample is 1.5 or more of the non-capture beads to 1 of the capture beads, and a step of acquiring information on whether or not a subject from which the biological sample is collected has Alzheimer's disease, based on the intensity of the signal.

According to the first, third and fifth embodiments, phosphorylated tau protein in a biological sample can be detected. According to the second, fourth and sixth embodiments, it is possible to acquire information on whether or not the subject is Alzheimer's disease using the biological sample.

DETAILED DESCRIPTION OF THE PREFERRED EMBODIMENTS

Figure 1:
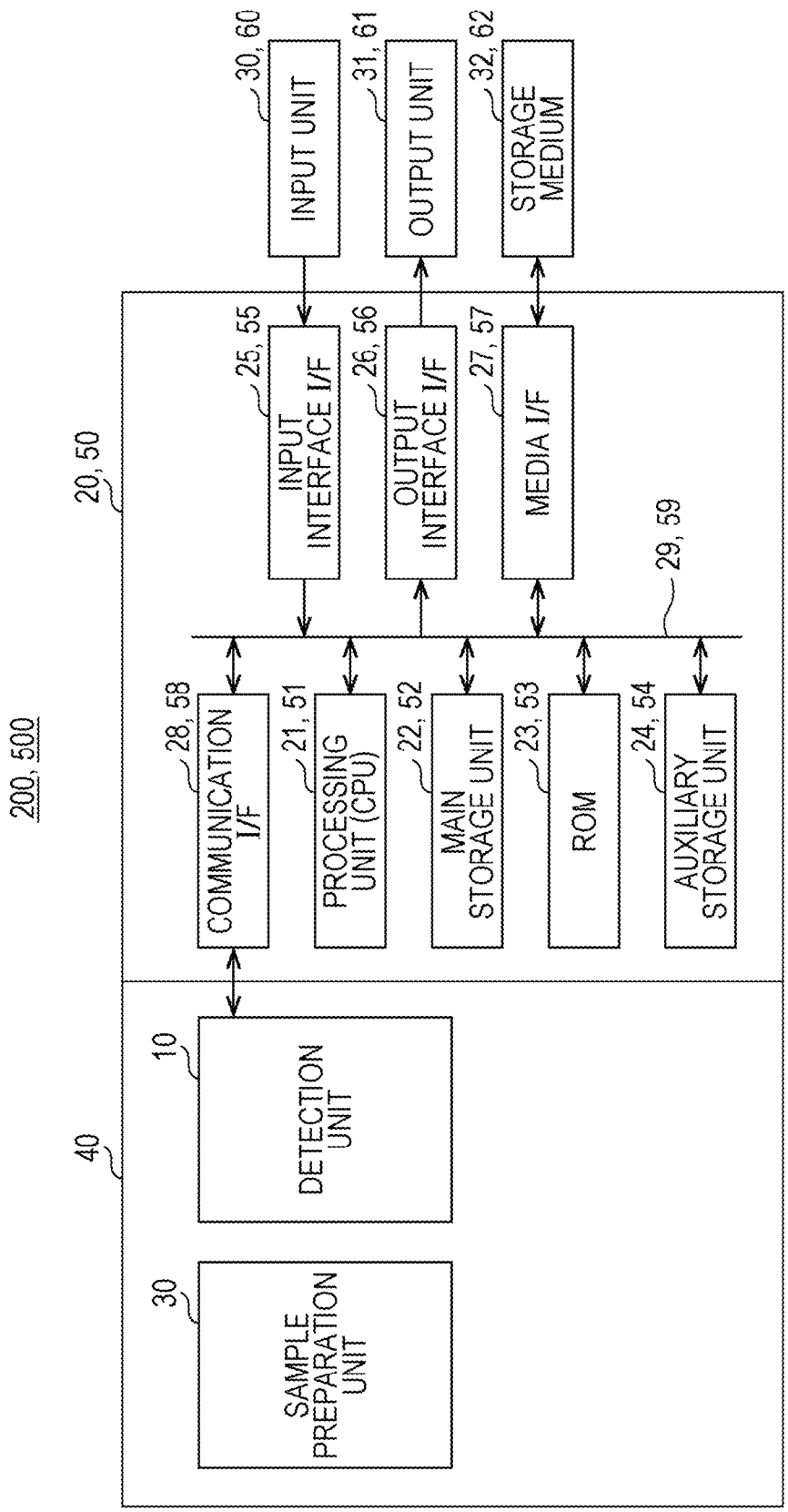
FIG. 1 is a diagram showing a configuration of a measuring device and an information acquisition device.

1. Method for Measuring Phosphorylated Tau Protein

The first embodiment relates to a method for measuring phosphorylated tau protein in a biological sample collected from a subject.

1-1. Explanation of Terms

First, terms used in this embodiment will be described. The description of the terms used in this embodiment is also incorporated in the description of other embodiments.

The subject is not particularly limited and may be a healthy person or a person who is not suspected of degenerative disease of cognitive disorder or central nervous system. The subject may also be a person suspected of cognitive impairment or degenerative disease of the central nervous system. Those who are of a certain age group, for example, 30 years old or over, 40 years old or over, 50 years old or over, 60 years old or over, 70 years old or over, or 80 years old or over may also be the subjects.

A biological sample collected from a subject is not particularly limited as long as it can contain phosphorylated tau protein, and examples thereof include a cerebrospinal fluid, a blood sample, and the like. The blood samples include whole blood, plasma, serum, and the like. Preferably the blood sample is plasma or serum, and more preferably plasma. The plasma can be separated from whole blood collected in heparin salt (preferably sodium salt), citrate (preferably sodium salt), and ethylenediamine tetraacetic acid (EDTA) salt (preferably sodium salt or potassium salt). More preferably, the plasma is plasma separated from whole blood collected in EDTA salt or heparin salt.

The tau protein is Paired helical filament-tau, and examples of those derived from humans include proteins registered in UniProtKB/Swiss-Prot: P10636.5 (https://www.ncbi.nlm.nih.gov/protein/P10636, as of Jul. 15, 2017).

The phosphorylated tau protein is not limited as long as tau protein is phosphorylated. For example, the phosphorylation site is at least one serine residue selected from the group consisting of the 199th, 202nd, 214th, 262nd, 356th, 396th, 404th, 409th, 416th, 422nd, 519th, 516th and 717th and/or at least one threonine residue selected from the group consisting of 181st, 205th, 212nd, 217th, 231st and 534th of the amino acid sequence of the above accession number. Preferably, the phosphorylation site is at least one selected from the group consisting of threonine 181, serine 199, threonine 231, and serine 262.

The antibody is not limited as long as it can recognize tau protein and/or phosphorylated tau protein. The antibody that recognizes phosphorylated tau protein is preferably an antibody that specifically binds to phosphorylated tau protein (phosphorylated tau protein specific antibody that does not bind to unphosphorylated tau protein). The phosphorylated tau protein specific antibody (hereinafter also referred to as "p-tau specific antibody") may recognize the phosphorylated phosphorylation site of the tau protein, or may recognize the tau protein whose structure has changed with phosphorylation. More preferably, the p-tau specific antibody recognizes the phosphorylated phosphorylation site of the tau protein.

As the antibody, any of tau protein, phosphorylated tau protein, or a polyclonal antibody, a monoclonal antibody, and a fragment thereof (for example, Fab, F(ab)2, or the like) obtained by immunizing nonhuman animals using a part thereof as an antigen can be used. Also, immunoglobulin classes and subclasses are not particularly limited. Those selected from the antibody library by the phage display method or the like may be used.

As the antibody, commercially available antibody may be used. As the antibody recognizing tau protein, for example, Tau Monoclonal Antibody (clone: HT7, T46, TAU-5) from Thermo Fisher Scientific Inc. and the like can be used. Examples of the antibodies that recognize phosphorylated tau protein include Phospho-Tau (Thr181) Antibody (clone: 5HCLC), Phospho-Tau (Thr231) Polyclonal Antibody (Cat #: 710561), and Phospho-Tau (Ser214) Polyclonal Antibody (Cat #: 44-742G) from Thermo Fisher Scientific Inc. and the like can be used.

In the present specification, the capture antibody is an antibody that binds to the phosphorylated tau protein and is fixed on the bead described below. Fixation to the bead may be indirect fixation mediated by avidin (or streptavidin) and a substance such as biotin.

In the present specification, the detection antibody is an antibody that binds to the phosphorylated tau protein, and is preferably provided with a labeling substance described below.

At least one of the capture antibody and the detection antibody is a p-tau specific antibody. As a result, it is possible to specifically detect the phosphorylated tau protein among the tau proteins in the biological sample.

When a p-tau specific antibody is used as both the capture antibody and the detection antibody, it is preferred that epitopes of these antibodies are different.

When a p-tau specific antibody is used as one of the capture antibody and the detection antibody, the other antibody is preferably an antibody capable of binding to the tau protein regardless of the presence or absence of phosphorylation.

The beads are not limited as long as they have the property that the individual beads can be spatially separated. The beads may be provided in such a form that they can be spatially separated into a plurality of places (for example, wells). For example, the beads can be formed in a shape such as spherical, disk, ring, or cubic. The beads may be fine particles (for example, a plurality of particles suspended in a liquid), nanotubes, or the like.

The size or shape of the beads can be appropriately designed. For example, the shape of the beads includes sphere, cube, ellipsoid, tube, and the like. The average diameter of the beads (in the case of substantially spherical) or the average maximum cross-sectional dimension (in the case of other shapes) is more than about 0.1 µm, more than about 1 µm, more than about 10 µm, more than about 100 µm, or more than about 1 mm, or similar ones are included. The average diameter of the beads or the maximum outer dimension of the beads is about 0.1 µm to about 100 µm, about 1 µm to about 100 µm, about 10 µm to about 100 µm, between about 0.1 µm and about 1 mm, between about 1 µm and about 10 mm, between about 0.1 µm and about 10 µm, or the like. The average diameter or average maximum cross-sectional dimension of the beads used in this embodiment is the arithmetic mean of the diameter/maximum cross-sectional dimension of the beads.

The average maximum cross-sectional dimension of the beads can be measured using, for example, laser light scattering, microscopy, sieve analysis, electrical resistance method, or other known techniques. The average diameter of the beads is a volume-based median diameter measured with a particle size distribution measuring device by laser diffraction/scattering method. Examples of the particle size distribution measuring device include "Microtrac MT3000 II" manufactured by NIKKISO CO., LTD., and the like.

The beads are insoluble or substantially insoluble in the solvent or solution used in the measurement. The beads may be porous or substantially porous, hollow, partially hollow, or the like, but are preferably non-porous solids or substantially non-porous solids (for example, essentially free of pores). The beads may be one that substantially absorbs or absorbs the solvent, but preferably nonabsorb, or substantially nonabsorb the solvent.

As the material of the beads, a plastic or a synthetic polymer (such as polyethylene, polypropylene, polystyrene, polyamide, polyurethane, phenol polymer or nitrocellulose), a naturally occurring polymer (including latex rubbers, polysaccharide metals, or metal compounds (such as gold, silver, steel, aluminum, and copper), and the like), inorganic glass, silica, a mixture thereof, and the like can be selected. The beads preferably include a magnetic material. The beads are preferably optically detectable.

As the beads, commercially available beads can be used. For example, carboxyl-functionalized paramagnetic beads from Agilent Technologies (2.7 µm in diameter) can be used.

Capture beads are beads capable of immobilizing a complex containing tau protein and/or phosphorylated tau protein (hereinafter also referred to as "target protein"). For example, capture beads can be obtained by directly or indirectly fixing a molecule capable of binding to a target protein (hereinafter also referred to as "capture molecule") to the aforementioned beads. As the capture molecule, the capture antibody described above is exemplified.

The method for preparing the capture beads is not limited as long as the capture molecules can be bound to the beads. For example, when the capture molecule is an antibody, the capture beads can be prepared by the method described in WO 2016/115256 A. The capture beads may be prepared using a commercially available kit such as the Simoa™ Homebrew Assay Development kit from Quanterix Inc. The capture beads may be blocked with bovine serum albumin (BSA) or the like to suppress nonspecific binding.

Non-capture beads are beads that do not substantially bind to the target protein. The non-capture beads do not have capture molecules. The material of the beads used for the non-capture beads may be the same as the beads used for the capture beads, or may be different. As the non-capture beads, for example, Dye-Encoded Helper Beads from Quanterix Inc. may be used. The non-capture beads may be blocked with BSA or the like to suppress nonspecific binding.

1-2. Measurement Method

Next, the measurement method of this embodiment will be described.

This embodiment is a sandwich immunoassay method of forming a sandwich immune complex containing phosphorylated tau protein and detecting phosphorylated tau protein. This embodiment includes steps of preparing a measurement sample containing a non-capture bead and a capture bead to which an immune complex is bound, by forming the immune complex of the phosphorylated tau protein that is a target protein in the biological sample collected from a subject, a capture antibody and a detection antibody on the capture bead, in the presence of the non-capture bead, and detecting a signal derived from the immune complex in the measurement sample.

In this embodiment, the method of forming an immune complex of the target protein in the biological sample, the capture antibody and the detection antibody on the capture bead is not limited as long as this embodiment can be realized by the method. It is preferred that the capture antibody and the detection antibody recognize different epitopes of the target protein. For example, first, the target protein in the biological sample is bound to the capture antibody using a capture antibody that recognizes tau protein as a capture molecule on the capture bead, to bind (preferably, capture) the target protein on the capture bead. Next, a detection antibody that recognizes phosphorylated tau protein is bound to the phosphorylated tau protein contained in the target protein captured by the capture antibody to form an immune complex. Alternatively, for example, first, the target protein in the biological sample is bound to the capture antibody using a capture antibody that recognizes phosphorylated tau protein as a capture molecule on the capture bead, to bind (preferably, capture) the target protein on the capture bead. Next, a detection antibody that recognizes tau protein is bound to the phosphorylated tau protein captured by the capture antibody to form an immune complex. The biological sample may be diluted with, for example, 1 to 5×PBS containing 0.05% (v/v) to 0.15% polyethylene glycol sorbitan monolaurate (Tween (registered trademark)-20) and the like and used.

In another embodiment, an immune complex of phosphorylated tau protein in the biological sample, a capture antibody and a detection antibody may be formed in a buffer solution and then bound to the capture bead. For example, an immune complex can be fixed on the capture bead by bringing a bead on which avidin or streptavidin is immobilized into contact with a complex of a biotin-labeled capture antibody, phosphorylated tau protein and a detection antibody.

The immune complex is formed in the presence of a non-capture bead. The number ratio of the capture beads and the non-capture beads in preparing the measurement sample is about 1.5 or more when taking the capture beads as 1, and the number ratio of the non-capture beads can be adjusted to preferably in the range of about 1.5 to about 9, more preferably in the range of about 4 to about 9, and most preferably around 4. In another embodiment, the number ratio of the capture beads and the non-capture beads in preparing the measurement sample is about 1.5 or more when taking the capture beads as 1, and the number ratio of the non-capture beads is in the range of 1.5 or more, preferably in the range of 1.5 to 9, more preferably in the range of 4 to 9, and most preferably 4. The number of whole beads mixed with the biological sample or diluted biological sample can be adjusted to, for example, about 100,000 to 1,000,000, and preferably about 400,000 to 800,000, based on 100 µl of the biological sample or diluted biological sample.

Preparation of the measurement sample can be carried out in a buffer solution (for example, 1 to 5×PBS) capable of forming an immune complex. The buffer solution may contain a surfactant such as Tween (registered trademark)-20 in the order of 0.05% (v/v) to 0.15% (v/v). During the preparation of the measurement sample, the phosphorylated tau protein in the biological sample is captured by the capture antibody, and then the capture beads may be washed with the buffer solution before binding the detection antibody. The capture beads may be washed with the buffer solution even after forming an immune complex of the phosphorylated tau protein in the biological sample, the detection antibody, and the capture antibody on the capture bead.

The detection antibody can be added so as to have a final concentration of about 0.05 µg/ml to 1 µg/ml and 0.1 µg/ml to 0.5 µg/ml, based on 100 µl of the biological sample or the diluted biological sample. The detection antibody is preferably provided with a labeling substance.

Detection of the phosphorylated tau protein can be carried out by detecting a labeling substance contained in the immune complex. The labeling substance is not particularly limited as long as a detectable signal is generated. For example, it may be a substance which itself generates a signal (hereinafter also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes. Examples of the enzymes include alkaline phosphatase, peroxidase, β-galactosidase, luciferase, and the like. Examples of the fluorescent substances include fluorescent dyes such as fluorescein isothiocyanate (FITC), rhodamine and Alexa Fluor (registered trademark), fluorescent proteins such as GFP, and the like. Examples of the radioisotopes include $^{125}I$, $^{14}C$, $^{32}P$, and the like. Among them, an enzyme is preferable as a labeling substance, and β-galactosidase is particularly preferable.

The substrate of the enzyme can be appropriately selected from known substrates according to the type of the enzyme. For example, when alkaline phosphatase is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.13,7]decan]-4-yl)phenyl phosphate) and CSPD (registered trademark) (disodium 3-(4-methoxyspiro[1,2-dioxetane-3,2-(5'-chloro)tricyclo[3.3.1.13,7]decan]-4-yl)phenyl phosphate), and chromogenic substrates such as 5-bromo-4-chloro-3-indolyl phosphate (BCIP), disodium 5-bromo-6-chloro-indolyl phosphate, and p-nitrophenyl phosphate. When β-galactosidase is used as an enzyme, resorufin β-D-galactopyranoside can be used. When peroxidase is used as an enzyme, SuperSignal ELISA series from Thermo Fisher Scientific Inc. and the like can be used. The enzyme reaction is preferably carried out before arranging a bead in a microwell as described later, but the enzymatic reaction may be carried out after arranging the bead in the microwell.

The detection antibody is biotinylated beforehand and bound to the avidin or streptavidin labeled with the labeling substance, then the signal may be detected.

Signal detection can be performed on all or a part of the beads including the capture beads and the non-capture beads contained in the measurement sample. Signal detection is preferably performed on individual beads. Since the presence or absence, intensity, wavelength and the like of the signal are different between the capture bead and the non-capture bead, it is preferable to use a detection device capable of distinguishing these beads.

As a method for detecting the signal of individual beads, for example, when the signal is fluorescence, it can be detected using a flow cytometer.

In another embodiment, the measurement sample may be brought into contact with a substrate having a plurality of microwells, the capture beads and the non-capture beads in the measurement sample may be arranged in the microwell, and a signal in the microwell may be detected.

On the substrate, the microwells can be arranged on a substantially flat surface or in a non-planar three dimensional array. The microwells may be arranged in a regular pattern or randomly distributed. The microwells are preferably in a regular pattern of sites on a substantially flat surface.

The number of microwells contained in the substrate can be about 1000 to 1,000,000 per one measurement sample. The substrate can contain preferably 10,000 to 500,000, and more preferably about 100,000 to 500,000 microwells.

The substrate material may be configured by glass (including modified and/or functionalized glass), plastic (polypropylene, polyethylene, polybutylene, polyurethane, cyclic olefin copolymer (COC), cyclic olefin polymer (COP), Teflon (registered trademark), polysaccharide, nylon, nitrocellulose, and the like), elastomer (for example, dimethylsiloxane, polyurethane, and the like), a composite material, a ceramic, silica or a silica-based material (including silicon and modified silicon), carbon, a metal, an optical fiber bundle, and the like.

The capacity of each microwell can be appropriately set according to the size of the beads. For example, the number of beads stored in one well is about 1 to 5, preferably about 1 to 2, and more preferably 1. Therefore, the volume of the microwell is preferably such that the number of beads described above can be stored in one well. (For example, US 2011/0212848 A, WO 2011/109364 A). More specifically, the volume of the microwell ranges from 100 attritor to 1 picoliter, preferably 1 femtoliter to 500 femtoliter, and more preferably 10 femtoliters to 90 femtoliter. It is preferable that the plurality of microwells present on one substrate have substantially the same volume.

The method of forming the microwell is not limited as long as a microwell of a desired size can be formed. For example, the microwell can be formed by a known method such as photolithography, stamping technique, molding technique, and etching technique.

The arrangement of the beads in the microwells can be carried out using a known method. For example, beads can be arranged in the microwells using the microfluidic technique described in WO 2016/115256 A. The beads may be arranged in all the microwells on the substrate or may be arranged in a part.

For example, the beads can be arranged in the microwells by bringing the measurement sample into contact with the substrate on which the microwell is designed, then centrifuging the substrate and the solution. When the beads are magnetic, the beads may be arranged in the microwells using a magnet. Alternatively, when the microwell is formed at the end of the optical fiber bundle, the beads may be arranged in the microwells by bringing the measurement sample into contact with around the other end of the optical fiber, then applying a force such as centrifugal force or pressure.

After arranging the beads in the microwells, the measurement sample remaining on the substrate surrounding the microwells may be removed, and the surface of the substrate may be washed and/or wiped to remove the excess measurement sample.

As the substrate containing the microwells, for example, Simoa™ Disk from Quanterix Inc. can be used.

The microwells after arranging the beads may be sealed with a fluorous liquid, an oil (for example, a mineral oil, a fluorinated oil), a ferrofluid, a non-aqueous polymer solution (for example, a thickener), or the like. For example, Simoa™ Sealing Oil from Quanterix Inc. may be used as the seal.

For example, when the labeling substance is an enzyme or a fluorescent dye, detection of the beads arranged in the microwells can be performed by imaging a signal with a CCD camera or the like. When the labeling substance is a radioactive isotope, the beads can be detected using autoradiography.

The beads arranged in the microwells are capture beads or non-capture beads, but capture beads that have captured the target protein emit a signal derived from the labeling substance (i.e., a signal derived from the immune complex), whereas beads that have not captured the target protein and non-capture beads do not emit a signal derived from the labeling substance. Therefore, by counting the number of wells that emit a signal derived from the labeling substance, the target protein can be quantified. The microwell for detecting a signal may be all or a part of the microwells on the substrate.

The number of wells that emit a signal derived from the labeling substance can be measured with, for example, Simoa™ HD-1 Analyzer from Quanterix Inc. When using the Simoa™ HD-1 Analyzer, the intensity of the signal is expressed as the average enzyme (AEB) value per bead. Therefore, the AEB value may be the signal intensity derived from the immune complex in the measurement sample.

Using the calibration curve, the AEB value may be converted into the measured value of phosphorylated tau protein. The measured value of phosphorylated tau protein refers to a value reflecting the amount or concentration of phosphorylated tau protein. When the measured value is indicated by "amount", it may be expressed on either a mole basis or a mass basis, but it is preferable to indicate the amount on a mass basis. When the value is expressed in terms of "concentration", it may be a molar concentration or a ratio (mass/volume) of a mass per constant volume of a biological sample, but the value is preferably expressed in terms of a ratio of mass/volume.

As a measurement method of this embodiment, it is preferable to use β-galactosidase as a labeling substance and resorufin β-D-galactopyranoside as a substrate according to the protocol from Quanterix Inc. Beads are applied to Simoa™ Disk, and it is preferable to obtain signal intensity with Simoa™ HD-1 Analyzer.

2. Method for Acquiring Information on Whether or Not Subject Suffers from Alzheimer's Disease In the second embodiment, information on whether or not the subject suffers from Alzheimer's disease is acquired, based on the intensity of the signal of the phosphorylated tau protein obtained in 1. above.

More specifically, the signal intensity derived from the phosphorylated tau protein in the biological sample of the subject is compared with a predetermined reference value, and when the signal intensity derived from the phosphorylated tau protein in the biological sample of the subject is high, information that the subject suffers from Alzheimer's disease is acquired.

The predetermined reference value refers to a reference value of the signal intensity derived from the phosphorylated tau protein. The reference value can be determined based on the signal intensity (negative control value) derived from the phosphorylated tau protein in a biological sample of a person who has not developed Alzheimer's disease and/or mild dementia. Alternatively, it can be determined based on the signal intensity (positive control value) derived from the phosphorylated tau protein in a biological sample of a person who has developed Alzheimer's disease. The reference value may be determined from both the negative control value and the positive control value. For example, a plurality of positive control values and a plurality of negative control values are acquired, and a value that can most accurately classify positive and negative based on these plural values can be taken as "reference value". The phrase "the value that can most accurately classify" can be appropriately set based on indices such as sensitivity, specificity, positive predictive value, negative predictive value, and the like, depending on the purpose of the examination. In another example, it is possible to set a reference value that can most accurately classify positive and negative from the viewpoint of sensitivity, specificity, negative predictive value, positive predictive value, and the like.

Information on whether or not the subject suffers from Alzheimer's disease may be acquired, using the measured value of phosphorylated tau protein, in place of the signal intensity.

3. Device for Measuring Phosphorylated Tau Protein, Device for Acquiring Information on Whether or Not Subject is Alzheimer's Disease The third embodiment relates to a device (hereinafter referred to as a measuring device) 20 for measuring phosphorylated tau protein in a biological sample collected from a subject, which includes at least a processing unit 21. The third embodiment may be a system 200 for measuring phosphorylated tau protein in a biological sample collected from a subject, which includes a measuring device 20 and a measurement unit 40.

The fourth embodiment relates to a device (hereinafter referred to as information acquisition device) 50 for acquiring information on whether or not the subject is Alzheimer's disease, based on the signal intensity of phosphorylated tau protein in a biological sample collected from a subject, which includes at least a processing unit 51. The fourth embodiment may be a system 500 for acquiring information on whether or not the subject is Alzheimer's disease, based on the signal intensity of phosphorylated tau protein in a biological sample collected from a subject, which includes the information acquisition device 50 and the measurement unit 40.

In the third and fourth embodiments, while explanation of the terms already explained in the above sections 1. and 2. is omitted, explanation of each term in the above sections 1. and 2. is also incorporated in the second embodiment.

3-1. Configuration of Measuring Device

FIG. 1 shows a hardware configuration of the measuring device 20. The measuring device 20 may be connected to an input unit 30, an output unit 31, and a storage medium 32.

In the measuring device 20, a processing unit (CPU) 21, a main storage unit 22, a ROM (read only memory) 23, an auxiliary storage unit 24, a communication interface (I/F) 28, an input interface (I/F) 25, an output interface (I/F) 26 and a media interface (I/F) 27 are data-communicably connected with each other via a bus 29.

The CPU 21 is a processing unit of the measuring device 20. The CPU 21 executes a computer program stored in the auxiliary storage unit 24 or the ROM 23 and processes data to be acquired so that the measuring device 20 functions.

The ROM 23 is configured by a mask ROM, a PROM, an EPROM, an EEPROM, and the like, and a computer program executed by the CPU 21 and data used for the computer program are recorded in the ROM 23. The CPU 21 may be an MPU 21. When starting the measuring device 20, the ROM 23 stores a boot program executed by the CPU 21 and programs and settings related to the operation of the measuring device 20 hardware.

The main storage unit 22 is configured by a RAM (Random Access Memory) such as SRAM or DRAM. The main storage unit 22 is used for reading the computer program recorded in the ROM 23 and the auxiliary storage unit 24. The main storage unit 22 is used as a work area when the CPU 21 executes these computer programs.

The auxiliary storage unit 24 is configured by a semiconductor memory element such as a hard disk and a flash memory, an optical disk, and the like. In the auxiliary storage unit 24, various computer programs to be executed by the CPU 21, such as operating systems and application programs, and various setting data used for executing computer programs are stored. Specifically, the auxiliary storage unit 24 stores a measurement program to be described later, a reference value of signal intensity, a reference value of measured values of phosphorylated tau protein, and the like.

The communication I/F 28 is configured by a serial interface such as USB, IEEE1394 and RS-232C, a parallel interface such as SCSI, IDE, and IEEE1284, an analog interface including a D/A converter and an A/D converter, a network interface controller (Network interface controller: NIC), and the like. Under the control of the CPU 21, the communication I/F 28 receives the data from the measurement unit 40 or another external device, and the communication I/F 28 transmits or displays information stored in or generated by the measuring device 20 as necessary to the measurement unit 40 or to the outside. The communication I/F 28 may communicate with the measurement unit 40 or another external device via a network.

The input I/F 25 is configured by, for example, a serial interface such as USB, IEEE1394, and RS-232C, a parallel interface such as SCSI, IDE, and IEEE1284, an analog interface including a D/A converter an A/D converter, and the like. The input I/F 25 receives character input, click, voice input and the like from the input unit 30. The received input content is stored in the main storage unit 22 or the auxiliary storage unit 24.

The input unit 30 is configured by a touch panel, a keyboard, a mouse, a pen tablet, a microphone, and the like. The input unit 30 performs character input or voice input to the measuring device 20. The input unit 30 may be connected from the outside of the measuring device 20 or integrated with the measuring device 20.

The output I/F 26 is configured by, for example, the same interface as the input I/F 25. The output I/F 26 outputs the information generated by the CPU 21 to the output unit 31. The output I/F 26 outputs the information generated by the CPU 21 and stored in the auxiliary storage unit 24 to the output unit 31.

The output unit 31 is configured by, for example, a display, a printer, and the like. The output unit 31 displays the measurement results transmitted from the measurement unit 40, various operation windows in the measuring device 20, measurement results, and the like.

The media I/F 27 reads, for example, application software or the like stored in the storage medium 32. The read application software or the like is stored in the main storage unit 22 or the auxiliary storage unit 24. The media I/F 27 writes the information generated by the CPU 21 in the storage medium 32. The media I/F 27 writes the information generated by the CPU 21 and stored in the auxiliary storage unit 24 to the storage medium 32.

The storage medium 32 is configured by a flexible disk, CD-ROM, DVD-ROM, or the like. The storage medium 32 is connected to the media I/F 27 by a flexible disk drive, a CD-ROM drive, a DVD-ROM drive, or the like. In the storage medium 32, an application program or the like for allowing the computer to execute operation may be stored.

The CPU 21 may acquire application software and various settings necessary for controlling the measuring device 20 via a network, instead of reading from the ROM 23 or the auxiliary storage unit 24. The application program is stored in the auxiliary storage unit 24 of the server computer on the network, and it is also possible that the measuring device 20 accesses the server computer to download the computer program and store it in the ROM 23 or the auxiliary storage unit 24.

In the ROM 23 or the auxiliary storage unit 24, an operation system for providing a graphical user interface environment such as Windows (registered trademark) manufactured and sold by Microsoft Corporation may be installed. It is assumed that the application program according to the fifth embodiment operates on the operating system. That is, the measuring device 20 may be a personal computer or the like. The measuring device 20 may be incorporated in the measurement unit 40.

3-2. Configuration of Information Acquisition Device

FIG. 1 shows a hardware configuration of the information acquisition device 50. The information acquisition device 50 may be connected to an input unit 60, an output unit 61, and a storage medium 62.

In the information acquisition device 50, a processing unit (CPU) 51, a main storage unit 52, a ROM (read only memory) 53, an auxiliary storage unit 54, a communication interface (I/F) 58, an input interface (I/F) 55, an output interface (I/F) 56 and a media interface (I/F) 57 are data-communicably connected with each other via a bus 59.

For the details of each configuration, the explanation of each corresponding configuration described in 3-1. above is incorporated herein by reference.

3-3. Configuration of Measurement Unit

The measurement unit 40 may include a detection unit 10 provided with an imaging device such as a CCD camera for detecting at least a signal, and may further include a sample preparation unit 30 for preparing a measurement sample in some cases. The detection unit 10 may be a flow cytometer. The detection unit 10 may include a pressurizing device, a depressurizing device, or a centrifugal device (not shown) for arranging beads in a measurement sample in microwells.

The measurement unit 40 may be integrated with the measuring device 20 or the information acquisition device 50. Examples of a device which is provided with an imaging unit in the detection unit 10 and integrated with the measuring device 20 or the information acquisition device 50 include Simoa™ HD-1 Analyzer.

3-4. Operation of Measuring Device, Information Acquisition Device

Figure 2:
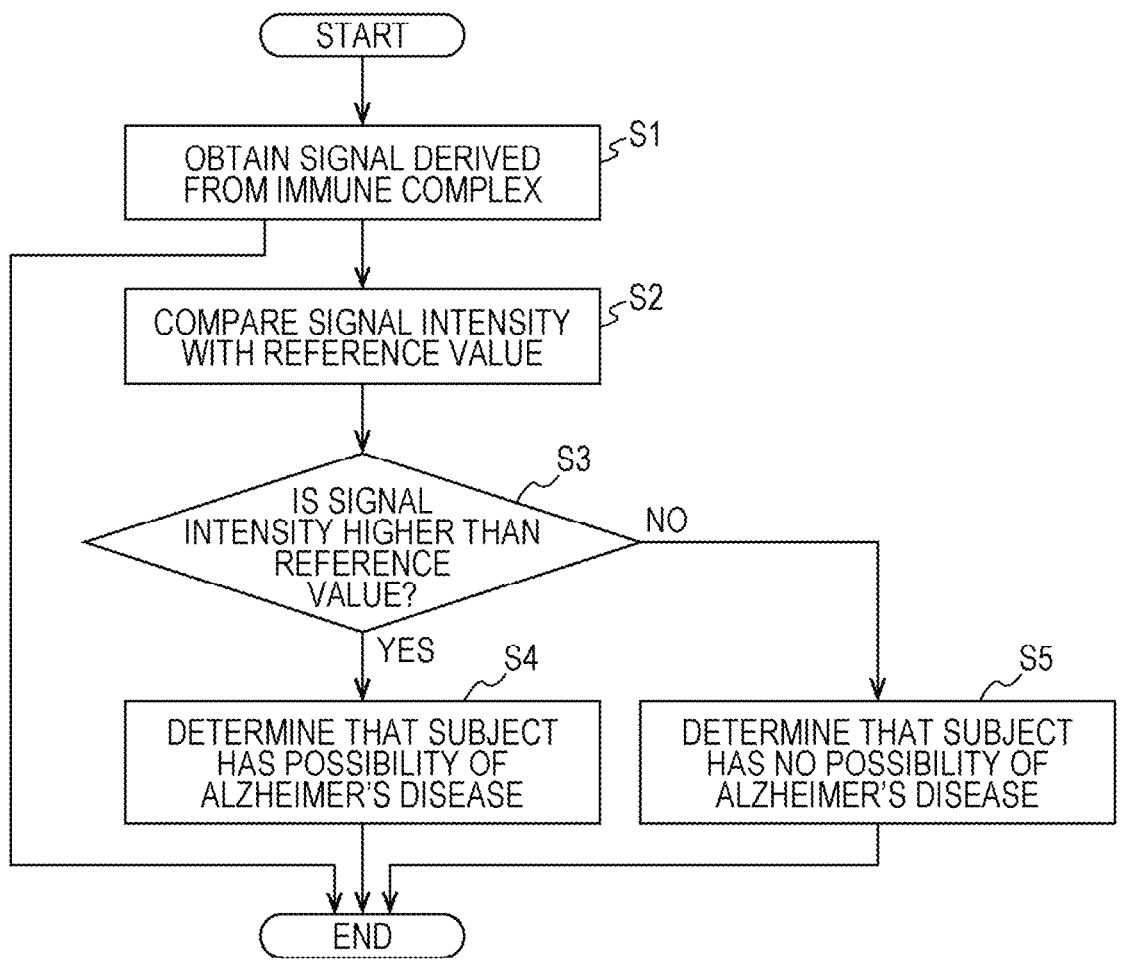
FIG. 2 is a diagram showing a flowchart of the operation of the measuring device and the information acquisition device.

The operation of the measuring device 20 will be described with reference to FIG. 2. The measuring device 20 is controlled by the processing unit 21 in accordance with a measurement program to be described later.

First, the processing unit 21 receives an input for obtaining a signal derived from the immune complex, for the measurement sample, performed from the input unit 30 by the examiner (not shown). Next, a signal derived from the immune complex detected by the measurement unit 40 is obtained (step S1). The processing unit 21 stores the intensities of these obtained signals in the auxiliary storage unit 54 or the like.

Next, the operation of the information acquisition device 50 will be described with reference to FIG. 2. The information acquisition device 50 is controlled by the processing unit 51 in accordance with an information acquisition program to be described later.

First, the processing unit 51 receives an input for obtaining a signal derived from the immune complex, for the measurement sample, performed from the input unit 60 by the examiner (not shown). Next, a signal derived from the immune complex detected by the measurement unit 40 is obtained (step S1). Subsequently, the reference value of the signal intensity stored in the auxiliary storage unit 54 or the like is compared with the obtained signal intensity (step S2). When the signal obtained for the measurement sample is higher than the reference value in the comparison in step S2 (step S3), the processing unit 51 determines that the subject has a possibility of Alzheimer's disease (step S4). When the signal obtained for the measurement sample is lower than the reference value in the comparison in step S2 (step S3), the processing unit 51 determines that the subject has no possibility of Alzheimer's disease (step S4). The processing unit 51 stores these determination results in the auxiliary storage unit 54 or the like as information on whether or not the subject is Alzheimer's disease. The processing unit 51 may output these results to the output unit 61 or may store these results in the storage medium 62.

4. Computer Program for Measuring Phosphorylated Tau Protein, Computer Program for Acquiring Information on Whether or Not Subject is Alzheimer's Disease The fifth embodiment relates to a computer program (hereinafter referred to as measurement program) for measuring phosphorylated tau protein. Specifically, it is a measurement program for controlling the operation of the measuring device 20 described in 3-4. above. The step that the measurement program makes the computer execute is step S1 shown in FIG. 2. The explanation of each of the terms described in 1. and 2. above is incorporated herein by reference.

The sixth embodiment relates to a computer program (hereinafter referred to as an information acquisition program) for acquiring information on whether or not the subject is Alzheimer's disease. Specifically, it is a measurement program for controlling the operation of the information acquisition device 50 described in 3-4. above. The steps that the information acquisition program makes the computer execute are steps S1 to S5 shown in FIG. 2. The explanation of each of the terms described in 1. and 2. above is incorporated herein by reference.

The computer program according to the fifth and sixth embodiments may be stored in a semiconductor memory element such as a hard disk or a flash memory, or a storage medium such as an optical disk. The storage format of the program in the storage medium is not limited as long as the information acquisition device can read the program. Storage into the storage medium is preferably nonvolatile.

5. Reagents and Reagent Kit for Detection of Phosphorylated Tau Protein

Figure 3:
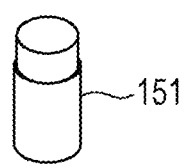
FIG. 3 is a view showing an outline of a reagent.

A seventh embodiment relates to a reagent for detecting phosphorylated tau protein. FIG. 3 shows a schematic view of a container 151 storing the reagent of this embodiment. The container 151 stores a reagent containing a liquid such as water or a buffer solution (for example, PBS), capture beads, and non-capture beads. The number ratio of the capture beads and the non-capture beads contained in the reagent is as described in 1-2. above.

Figure 4:
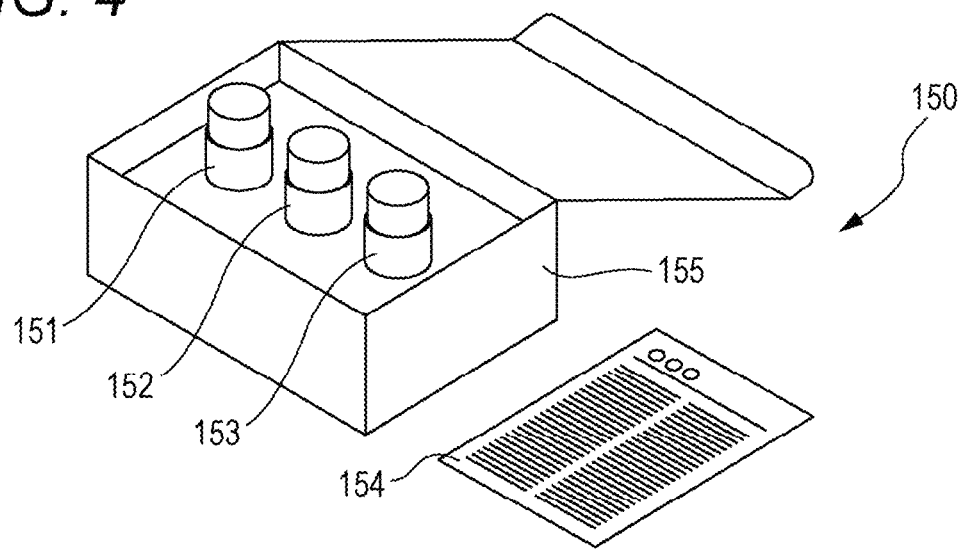
FIG. 4 is a view showing an outline of an example of a reagent kit.
Figure 5:
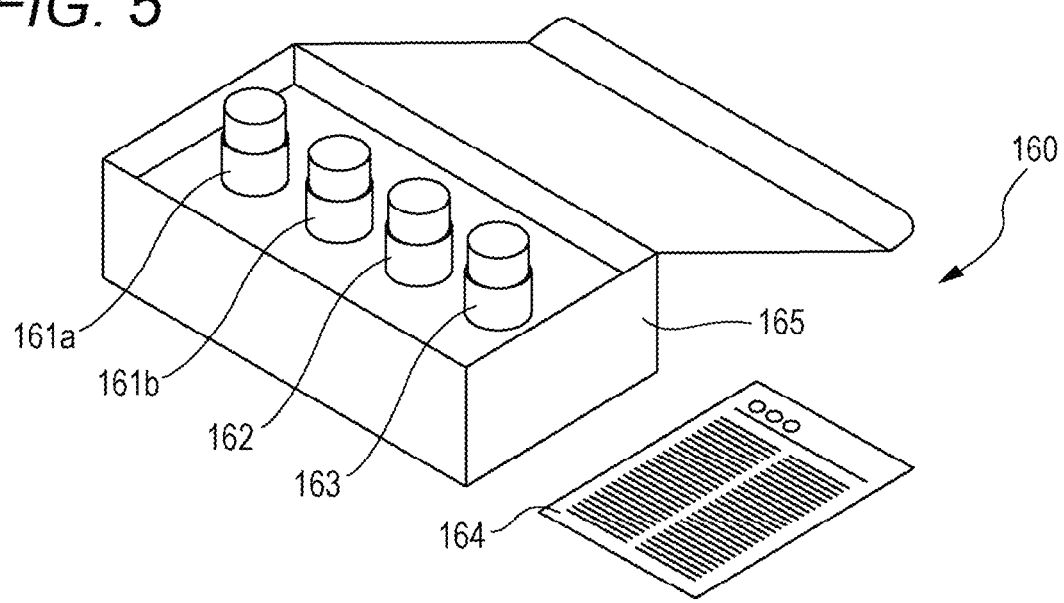
FIG. 5 is a view showing an outline of another example of the reagent kit.

An eighth embodiment relates to a reagent kit for detecting phosphorylated tau protein. FIGS. 4 and 5 show schematic views of the reagent kit 150 and the reagent kit 160 of this embodiment.

The reagent kit 150 that is an example of the eighth embodiment contains a container 151 and a container 152 storing a reagent (luminescent substrate or the like) for detecting phosphorylated tau protein. The reagent kit 150 may further contain a container 153 storing a reagent containing a detection antibody. When the capture antibody is not immobilized on the bead, the reagent kit 150 may further contain a reagent (not shown) containing the capture antibody. The reagent kit 150 may contain an instruction manual or a sheet 154 describing URL in which the instruction manual can be browsed. The reagent kit 150 may contain a box 155 containing these containers.

In a reagent kit 160 that is another example of the eighth embodiment, the capture beads and the non-capture beads are stored in separate containers 161a and 161b. The number ratio of the capture beads and the non-capture beads is as described above. The reagent kit 160 may further contain a container 162 storing a reagent (luminescent substrate or the like) for detecting phosphorylated tau protein and a container 163 storing a reagent containing a detection antibody. When the capture antibody is not immobilized on the bead, the reagent kit 160 may further contain a reagent (not shown) containing the capture antibody. The reagent kit 160 may contain an instruction manual or a sheet 164 describing URL in which the instruction manual can be browsed. The reagent kit 160 may contain a box 165 containing these containers.

Although each of the embodiments has been described in detail with reference to the attached drawings, the method for measuring phosphorylated tau protein in a biological sample, the method for acquiring information on whether or not a subject suffers from Alzheimer's disease, the device for measuring phosphorylated tau protein in a biological sample, the device for acquiring information on whether or not a subject suffers from Alzheimer's disease, the computer program for measuring phosphorylated tau protein in a biological sample, and the computer program for acquiring information on whether or not a subject suffers from Alzheimer's disease are not limited to the specific embodiments described above. Embodiments can be modified based on the description of this specification and technical common knowledge of those skilled in the art.

EXAMPLES

Hereinafter, the present disclosure will be described in more detail by way of examples, but the present disclosure is not to be construed as being limited to the examples.

1. Detection of Phosphorylated Tau Protein by ELISA Method (1) Preparation of Capture Beads and Biotin-Labeled Antibody Capture beads to which an antibody (capture antibody) for capturing a target protein is bound and biotin-labeled antibody (detection antibody) for detecting a target protein are prepared using Simoa™ Homebrew Assay Development Kit (Quanterix Inc.) according to the protocol attached to the kit. In the preparation, 1-ethyl-3-(3-dimethylaminopropyl) carbodiimide hydrochloride (EDC: Thermo Fisher Scientific Inc.), biotin (Thermo Fisher Scientific Inc.) and a centrifugal filtration filter (Merck Millipore) attached to the kit were used.

As antibodies, an antibody that recognizes tau protein aa.159-163 (Anti-Human Tau Monoclonal Antibody, Purified, clone: HT7; Thermo SCIENTIFIC Inc.) and an antibody that recognizes phosphorylation of Thr181 of phosphorylated tau protein (Anti-Human PHF-Tau Monoclonal Antibody, Purified, clone: AT270, Thermo SCIENTIFIC Inc.) were used. Hereinafter, the former is referred to as HT7 antibody, and the latter is referred to as AT270 antibody.

(2) Immunoassay

Measurement was carried out according to the manufacturer's protocol, using the capture beads prepared in the above (1) and the biotin-labeled antibody prepared in the above (1), Dye-Encoded Helper Beads (non-capture beads) from Quanterix Inc., Simoa™ Enzyme and Substrate kit, Simoa™ Disk kit, Simoa™ Sealing Oil, System buffer 1, System buffer 2, and Simoa™ HD-1 Analyzer. For the measurement, the measurement sample and necessary reagents such as the capture beads, the biotin-labeled antibody and the non-capture beads were set in the Simoa™ HD-1 Analyzer, and all measurement steps were performed with the Simoa™ HD-1 Analyzer.

Specific steps are as follows. Initially, a capture antibody bound to the capture bead was bound to a target protein, in the presence of the non-capture bead. Subsequently, the biotinylated detection antibody was further bound to the target protein bound to the capture antibody to form an immune complex of the capture antibody, the target protein and the biotinylated detection antibody on the capture bead. After the above steps, the capture beads were reacted with streptavidin to which β-galactosidase was bound in the presence of the non-capture bead. After the above steps, the capture beads were reacted with the substrate of β-galactosidase (RGP: resorufin β-D-galactopyranoside) in the presence of the non-capture bead. The capture beads and non-capture beads after reaction with RGP were applied to Simoa™ Disk. Thereafter, the applied beads were stored one by one in each well of the array in which a large number of femtoliter unit wells were arranged. Each bead stored in the well was photographed by Simoa™ HD-1 Analyzer, the fluorescence intensity (AEB) was measured, and the number of beads with high fluorescence intensity was measured to quantify the target protein.

2. Example 1

The optimal ratio of the capture beads to the non-capture beads was examined using HT7 antibody as a capture antibody and AT270 antibody as a detection antibody. The experiment was carried out according to the method described in the above 1. For examination, one obtained by diluting Hu Tau [pT181] Standard attached to Human Tau [pT181] phosphoELISA™ ELISA kit (Thermo Fisher Scientific Inc.) that is phosphorylated tau protein, to 0.039 pg/ml with Sample Diluent attached to Simoa™ Homebrew Assay Development kit was used as a sample for measurement. For one measurement, 152 μl of 0.039 pg/ml Hu Tau [pT181] Standard was used.

Figure 6:
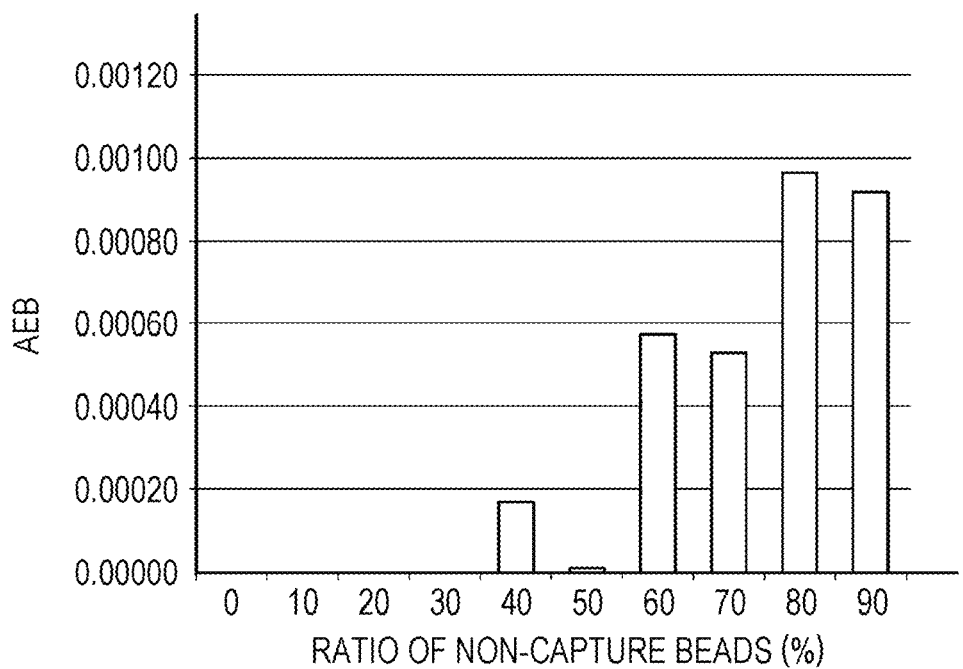
FIG. 6 is a graph in which an optimal ratio of the number of capture beads to the number of non-capture beads is examined by binding an anti-tau protein antibody to capture beads.

The AEBs were compared when 0.039 pg/ml pT181 was measured with changing the ratio of the non-capture beads to 10, 20, 30, 40, 50, 60, 70, 80 and 90%, based on 100% of the total of the capture beads and the non-capture beads. The results are shown in FIG. 6. As a result, a strong AEB was obtained when the non-capture beads were 60% or more.

Therefore, in order to detect phosphorylated tau protein, it was considered preferable to set the ratio of the capture beads to the non-capture beads in the range of 40:60 to 10:90, that is, in the range of 1:1.5 to 1:9. Furthermore, it was considered particularly preferable to set the ratio of the capture beads to the non-capture beads in the range of 20:80 to 10:90, that is, in the range of 1:4 to 1:9.

3. Example 2

Next, the optimal ratio of the capture beads to the non-capture beads was examined in the same manner as in Example 1, except for using AT270 antibody as a capture antibody and HT7 antibody as a detection antibody.

Figure 7:
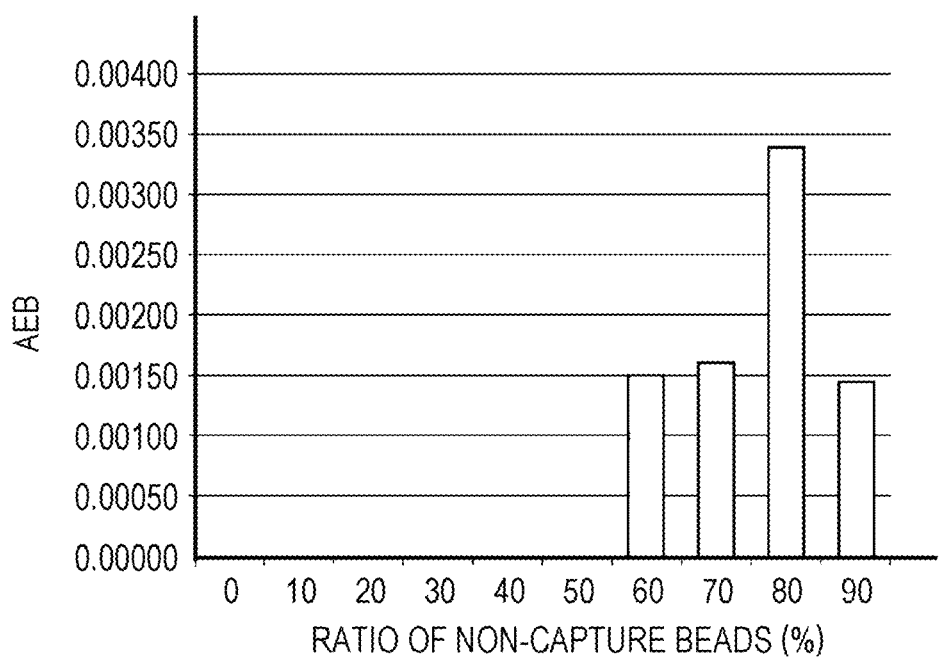
FIG. 7 is a graph in which an optimal ratio of the number of capture beads to the number of non-capture beads is examined by binding an anti-phosphorylated tau protein antibody to capture beads.
Figure 8:
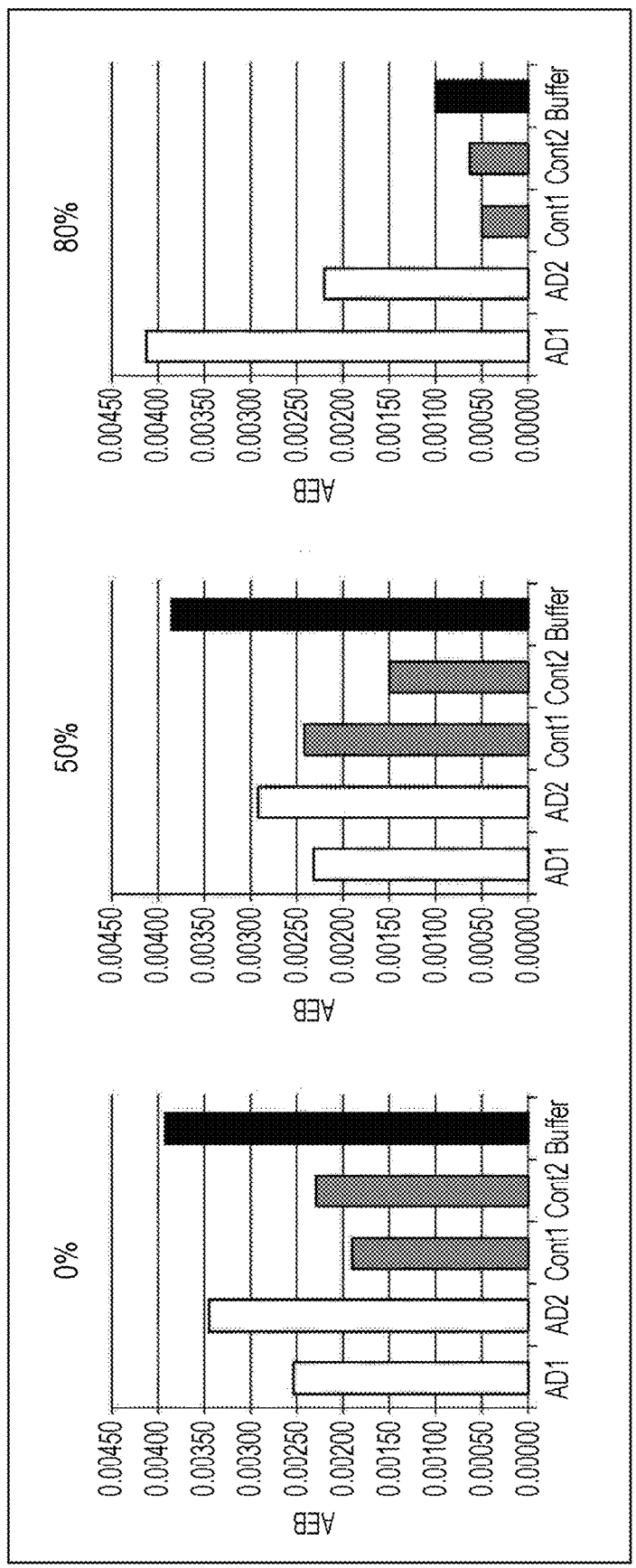
FIG. 8 is diagrams showing differences in detection rates of Alzheimer's disease patients depending on the ratio of capture beads and non-capture beads.

The AEBs were compared when 0.039 pg/ml pT181 was measured with changing the ratio of the non-capture beads to 10, 20, 30, 40, 50, 60, 70, 80 and 90%, based on 100% of the total of the capture beads and the non-capture beads. The results are shown in FIG. 7. As a result, a strong AEB was obtained when the non-capture beads were 60% or more.

Therefore, in order to detect phosphorylated tau protein, it was considered preferable to set the ratio of the capture beads to the non-capture beads in the range of 40:60 to 10:90, that is, in the range of 1:1.5 to 1:9.

4. Example 3

Next, the optimal ratio of the capture beads to the non-capture beads was examined using human plasma (EDTA-2Na blood collection) as a sample. The phosphorylated tau protein in plasma of 2 patients with Alzheimer's disease (AD1, AD2) and 2 control patients (Cont. 1, Cont. 2), in place of the diluted solution of Hu Tau [pT181], were measured. Plasma was diluted 4 times with Sample Diluent and measured. Buffer was used as a blank. Whether or not Alzheimer's disease patients could be detected was compared with changing the ratio of the non-capture beads to 0, 50, and 80%, based on 100% of the total of the capture beads and the non-capture bead.

The results are shown in FIG. 7.

When the ratio of the non-capture beads was set to 0% or 50%, it was not possible to distinguish between Alzheimer's disease patients and control patients, and Alzheimer's disease patients could be detected only when the ratio was set to 80%.

From the above results, it was considered preferable to set the ratio of the capture beads to the non-capture beads to be more than 1:1 when measuring phosphorylated tau protein using a biological sample, and detecting Alzheimer's disease patients.

What is claimed is:

1. A method for measuring phosphorylated tau protein in a biological sample collected from a subject, comprising the steps of:
    preparing a measurement sample by forming an immune complex of the phosphorylated tau protein in the biological sample, a capture antibody and a detection antibody on a capture bead, in the presence of a non-capture bead, wherein the measurement sample comprises the non-capture bead to which the immune complex does not bind and the capture bead to which the immune complex is bound, and wherein the capture antibody is not immobilized on the non-capture bead;
    detecting a signal derived from the immune complex in the measurement sample; and
    comparing said detected signal to a reference value, and determining that said test sample is from a subject with Alzheimer's disease based on the comparison,
    wherein at least one of the detection antibody and the capture antibody specifically recognizes the phosphorylated tau protein,
    an epitope of the capture antibody is different from an epitope of the detection antibody, and
    the number ratio of the capture beads and the non-capture beads mixed in the preparation step is 4 to 9 of the non-capture beads to 1 of the capture beads.

2. The method according to claim 1, wherein in the detection step, the phosphorylated tau protein is measured based on the signal.

3. The method according to claim 1, wherein, in the detection step,
    the measurement sample is brought into contact with a substrate having a plurality of microwells,
    the capture beads and the non-capture beads in the measurement sample are arranged one by one in the microwells, and
    a signal derived from the immune complex on the capture beads arranged in the microwells is detected,
    wherein the microwells have a volume capable of storing single capture bead or single non-capture bead.

4. The method according to claim 3, wherein in the detection step,
    the number of microwells comprising the capture bead on which the immune complex is formed or the number of capture beads on which the immune complex is formed in the microwell is calculated,
    the phosphorylated tau protein is measured based on the calculation result.

5. The method according to claim 1, wherein, in the detection step, signal detection is performed by imaging the signal derived from the immune complex.

6. The method according to claim 1, wherein the biological sample is a blood sample.

7. The method according to claim 6, wherein the blood sample is serum or plasma.

8. The method according to claim 1, wherein the immune complex is formed by mixing a capture antibody bound to the capture bead, a biological sample containing phosphorylated tau protein, and a detection antibody, in the presence of the non-capture bead.

9. The method according to claim 1, wherein the signal is a fluorescent signal.

10. The method of claim 1, wherein the capture antibody is able to specifically bind to the capture bead, and wherein the capture antibody is unable to specifically bind to the non-capture bead.

11. A method for measuring phosphorylated tau protein in a biological sample collected from a subject, comprising the steps of:
    preparing a measurement sample by forming an immune complex of the phosphorylated tau protein in the biological sample, a capture antibody and a detection antibody on a capture bead, in the presence of a non-capture bead, wherein the measurement sample comprises the non-capture bead to which the immune complex does not bind and the capture bead to which the immune complex is bound;
    detecting a signal derived from the immune complex in the measurement sample; and
    comparing said detected signal to a reference value, and determining that said test sample is from a subject with Alzheimer's disease based on the comparison,
    wherein the non-capture bead is a bead on which the capture antibody is not immobilized,
    at least one of the detection antibody and the capture antibody specifically recognizes the phosphorylated tau protein, and
    the number ratio of the capture beads and the non-capture beads mixed in the preparation step is 4 to 9 of the non-capture beads to 1 of the capture beads.

12. The method according to claim 11, wherein the biological sample is serum or plasma.

13. The method of claim 11, wherein the capture antibody is able to specifically bind to the capture bead, and wherein the capture antibody is unable to specifically bind to the non-capture bead.

\* \* \* \* \*